(12) United States Patent
Jacobson

(10) Patent No.: US 9,022,824 B2
(45) Date of Patent: May 5, 2015

(54) VARIABLE PITCH OARLOCK

(75) Inventor: Desmond William Jacobson, Brisbane (AU)

(73) Assignee: Oar Inspired Pty. Ltd., Brisbane, Queensland (AU)

( * ) Notice: Subject to any disclaimer, the term of this patent is extended or adjusted under 35 U.S.C. 154(b) by 276 days.

(21) Appl. No.: 13/500,781

(22) PCT Filed: Oct. 5, 2010

(86) PCT No.: PCT/AU2010/001308
§ 371 (c)(1),
(2), (4) Date: Jul. 16, 2012

(87) PCT Pub. No.: WO2011/041833
PCT Pub. Date: Apr. 14, 2011

(65) Prior Publication Data
US 2012/0276508 A1    Nov. 1, 2012

(30) Foreign Application Priority Data

Oct. 7, 2009  (AU) ................................ 2009101026

(51) Int. Cl.
*B63H 16/06* (2006.01)
*A61B 5/22* (2006.01)
(Continued)

(52) U.S. Cl.
CPC ................ *B63H 16/06* (2013.01); *A63B 69/06* (2013.01); *G01L 5/00* (2013.01); *G01L 5/0028* (2013.01); *G01L 5/0095* (2013.01); *G01L 5/133* (2013.01); *A61B 5/224* (2013.01)

(58) Field of Classification Search
CPC .... B63H 16/06; B63H 16/067; B63H 16/073; B63H 2016/063; A61B 5/22; A61B 5/224; A63B 69/06; A63B 2069/064; G01L 5/00; G01L 5/0028; G01L 5/0095; G01L 5/133

USPC ................ 440/101–110; 434/247; 482/72, 73
See application file for complete search history.

(56) References Cited

U.S. PATENT DOCUMENTS

| | | | | |
|---|---|---|---|---|
| 998,562 | A | * | 7/1911 | Young ........................... 440/107 |
| 2,504,461 | A | * | 4/1950 | Spichler ....................... 440/107 |

(Continued)

FOREIGN PATENT DOCUMENTS

| | | | |
|---|---|---|---|
| EP | 16270 | A1 * | 10/1980 |
| GB | 2405947 | B | 10/2005 |

(Continued)

OTHER PUBLICATIONS

International Preliminary Report of Patentability issued Aug. 22, 2011 in International Application No. PCT/AU2010/001308.

(Continued)

*Primary Examiner* — Ajay Vasudeva
(74) *Attorney, Agent, or Firm* — Knobbe Martens Olson & Bear, LLP

(57) ABSTRACT

An improved variable pitch oarlock of a rowing shell, including a gate for securing an oar, which is adapted to swivel about a vertical pin of a rigger of the rowing shell. The improvement residing in the inclusion of horizontal pivot means adapted to vary the horizontal angular displacement of the gate as it swivels about the vertical pin. In operation, the pitch of the oar blade can be correspondingly varied and accurately determined during all phases of the rowing stroke. The horizontal pin also provides the mounting for force sensors; ensuring horizontal and/or vertical forces can be measured. Also claimed is a method of coaching or training rowing crew(s), utilizing the variable pitch oarlock as herein described, wherein force, angle and depth measurements are taken and analyzed.

5 Claims, 4 Drawing Sheets

(51) Int. Cl.
*A63B 69/06* (2006.01)
*G01L 5/00* (2006.01)
*G01L 5/13* (2006.01)

(56) References Cited

U.S. PATENT DOCUMENTS

| | | | | |
|---|---|---|---|---|
| 2,519,621 | A | * | 8/1950 | Agner ............................ 440/107 |
| 3,191,203 | A | * | 6/1965 | McClay, Jr. .................... 440/107 |
| 3,335,439 | A | * | 8/1967 | McClay, Jr. .................... 440/107 |
| 4,352,667 | A | | 10/1982 | Neville |
| 7,114,398 | B2 | * | 10/2006 | Haines ............................ 73/779 |

FOREIGN PATENT DOCUMENTS

| | | |
|---|---|---|
| SU | 1650171 A1 | 5/1991 |
| WO | WO 91/08945 A1 | 6/1991 |

OTHER PUBLICATIONS

International Search Report issued Jan. 19, 2011 in International Application No. PCT/AU2010/001308.

* cited by examiner

VARIABLE PITCH OARLOCK

CROSS-REFERENCE TO RELATED APPLICATIONS

This application is a U.S. National Phase under 35 U.S.C. §371 of International Application No. PCT/AU2010/001308, filed Oct. 5, 2010, which claims priority to Australian Application Number 2009101026, filed Oct. 7, 2009 in the Australian Patent Office, each of which is hereby incorporated by reference in its entirety.

BACKGROUND

1. Field of the Invention

The present invention relates to the sport of competitive rowing, more particularly, but not exclusively to a variable pitch rowlock and a novel facility to accurately measure, if necessary, the forces generated from a single point in the rowlock.

2. Description of the Related Art

In competition rowing, in which performance largely depends on minute changes and the preparation of equipment, how the rowing force is transmitted from the individual to the blade of an oar is critical. Oarlocks that are currently in the market place, however, still present problems in terms of free play and the accurate location and support of the oar in the row-bed or gate.

In particular, current gate designs commonly include a fixed pitch which cannot be easily adjusted, thus resulting in the pitch typically being set at a compromised setting. This compromise is typically set to prevent the oar from getting stuck in the water at the end of the stroke, versus the oar washing out. Currently there is no way of setting the pitch to the optimal setting for all phases of the rowing stroke, often referred to as catch, drive, and exit in rowing terminology.

Some coaches or crews will attempt to lean the pin in or out by physically bending the pin so that the pitch in the middle of the stroke can be set differently to the catch or finish. This technique is very coarse and cumbersome and typically fails to provide the desired outcomes. It also deforms and damages the pin. There are some commercially available wedges to assist in leaning the pin over. An alternative method is to wedge a small coin or washer under one side of the pin before tightening up the retaining nut. Leaning the pin only provides 2 or 3 degrees of adjustment. Leaning the pin does not allow the pitch to be set independently at the catch and finish of the stroke.

In addition to the above, prior art gate designs do not lend themselves to measuring force because of primarily two reasons:

1. There is no way to decouple the force sensor from measuring the weight of the oar in the gate and separating the thrust of the oar being applied in a horizontal direction to the pin from the gravitational weight of the oar itself; and
2. Current pitch adjustment mechanisms have considerable free play resulting in inaccurate force measurements.

Force measurements are currently determined either by measuring the force of the feet into the shoes or by measuring the load on the pin. There have also been attempts to measure the strain on the oar. Measuring the force on the shoes provides no reference to where in the stroke the pressure was applied, and this measurement is only accurate for the leg drive, not for the back swing or arms. Further, measuring the load on the pin, measures the combined weight of the oar with the force being applied. Although both techniques are used, neither provides an accurate measurement of force being applied to propel the boat in the forward direction, and neither method provides a reference to the angular position of the oar (Catch, Dive and Finish). Both techniques are also complicated to set up and calibrate and are only implemented by the true elites in the sport, for example the Australian Institute of Sport (AIS).

Some force measurement systems address the issue of free play by removing the pitch adjustment altogether, and locking it at 4 degrees. This is not acceptable for elite level rowers and as a result these systems are seldom left on the boat.

The disadvantages of the prior art can be summarised as follows:

Bending the pin provides no graduated adjustment of pitch across each phase of the rowing stroke e.g. catch, legs, back, arms, tap down.

No accurate and reliable way to adjust all gates in the boat to the same pitch profile.

Pitch can not be set independently at the catch and finish of the stroke.

The technique is not repeatable with any real accuracy.

Current force measurements do not truly reflect the propulsion to the boat.

Measuring from the feet or strain on the oar provides no angular reference to indicate where in the stroke the force was applied.

Without being able to accurately measure the force/angles and length of the stroke it is not possible to properly tune the pitch of the blade for optimum performance.

The same applies to setting oar lengths, inboard and outboard, and feet locations.

Pitch adjustment without accurate measurement would require guess work and would not result in maximum performance.

Current nylon pitch adjusters are loose fitting resulting in a large noise component in any force measurement taken on the pin.

It is therefore an object of the invention to ameliorate some or all of the above disadvantages of the prior art by providing a novel and innovative variable pitch rowlock or to at least provide the public with a useful choice.

SUMMARY OF THE INVENTION

In one aspect therefore the invention resides in a variable pitch oarlock of a rowing shell, including in combination,
 a gate for securing an oar,
  the oarlock adapted to swivel about, a vertical pin of a rigger of the rowing shell, characterized in that the oar lock further comprises a horizontal pivot means specially adapted to vary the angular displacement of the gate as it swivels about the vertical pin,
  wherein in operation, the pitch of the oar blade can be correspondingly varied and accurately determined during all phases of the rowing stroke, and the horizontal pin also providing the mounting for the force sensor, ensuring only horizontal forces are measured.

Preferably, the horizontal pivot means comprises a horizontal hinge or pivot between the oar clamp of the rowlock and a vertical bearing assembly to allow the gate to pivot in the horizontal plane and to swivel about the vertical pin,
  the oar clamp including a cam follower in contact with a profiled cam or spacer, adapted to affect the horizontal displacement of the gate, wherein in operation,
  the profile of the cam allows the pitch of the rowlock to be precisely set thereby controlling blade angle at all phases of the rowing stroke.

Preferably, the hinge facilitating the gate to pivot horizontally comprises a pair of opposed pivot lugs emanating from or formed from the material of the oar clamp which pivot about a horizontal hinge pin passing through the pivot lugs and the bearing assembly located between the lugs.

Preferably, the force measurements are obtained via one or more force transducers connected to or associated with the hinge pin, thereby enabling accurate and true propulsive force measurement in the absence of other non-propulsive forces such as hydrodynamic lift or oar weight.

The horizontal pin also providing the mounting for a force sensor thereby ensuring only horizontal (i.e. propulsive) forces are measured.

In the alternative, force transducers may be associated with any part of the gate.

Preferably, the profiled cam is fabricated from a resilient polymeric material such as Teflon or high impact plastic.

In the alternative, the cam can be machined from a billet of lightweight metal such as aluminium or stainless steel.

A cam follower can be machined from phosphor-bronze or other suitable bearing material.

Preferably, the cams are interchangeable components and cams of different profiles can easily be removed and replaced according to a desired blade pitch pattern or selected to suit and/or improve the performance of an individual rower.

Suitably, the measuring apparatus includes accelerometers and/or strain gauges and/or position sensors connected to wireless transmission means.

Data from the measuring apparatus can be transmitted by telemetry or other means to a computer having suitable software to process the information.

In a coaching or training application of the invention, the force measurements are subject to computer analysis wherein uploaded crew(s) performance data is used to design or customise the cam profiles to maximise performance.

In another aspect, the invention resides in a method of coaching or training rowing crew(s) wherein force, angle and depth measurements are taken and analysed, and cams with different profiles interchanged to tune the boat for maximum performance for the particular crew and to design a coaching or training schedule according to an analysis of the measurements taken.

BRIEF DESCRIPTION OF THE DRAWINGS

In order for the invention to be better understood reference will now be made to the accompanying drawings, wherein.

DETAILED DESCRIPTION OF THE DRAWINGS

Figure 1:
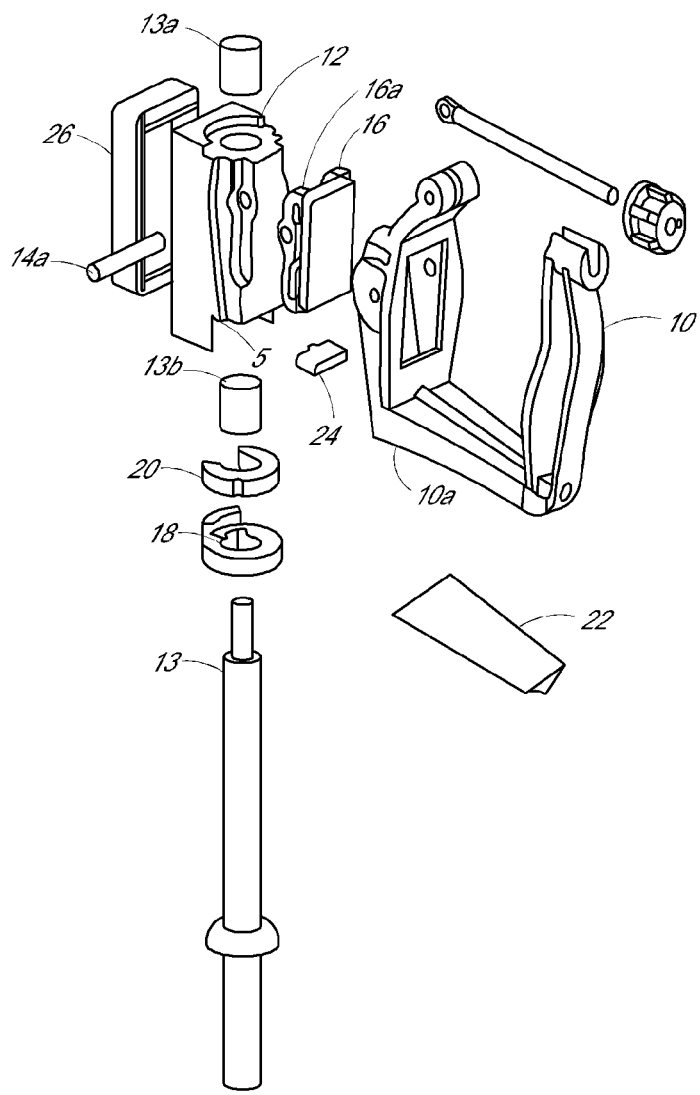
FIG. 1 shows a preferred rowlock according to the invention.
Figure 2A:
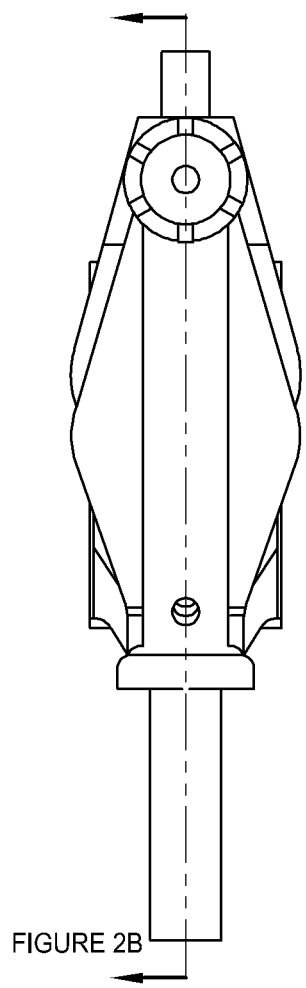
FIGS. 2A and 2B show front and side views of the rowlock of FIG. 1.
Figure 2B:
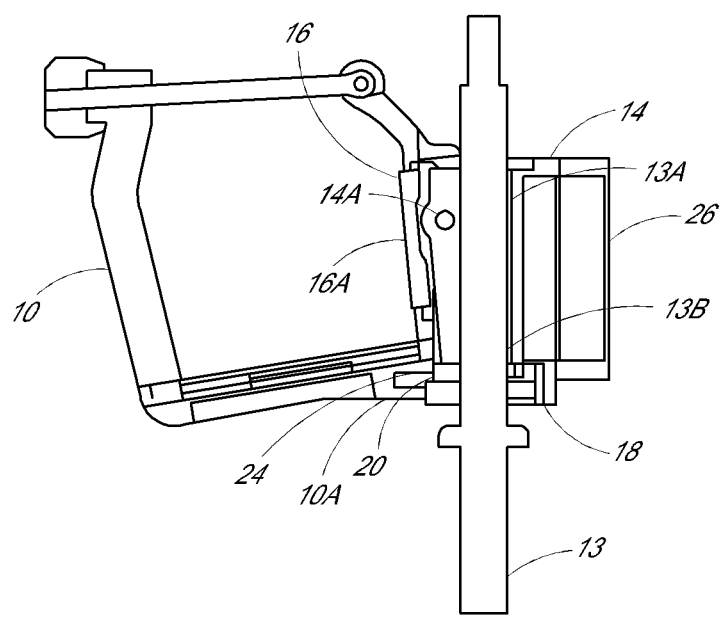

Referring now to the drawings and initially to FIG. 1 there is shown an exploded view of a preferred rowlock. FIGS. 2A and 2B show front and side views of the rowlock of FIG. 1.

The invention divides the gate or oar lock into two separate components. The vertical pivot 12 allowing the gate to rotate from catch to finish, and introduces an oar clamp 10 connected to vertical pivot by means of a horizontal pivot 14 allowing the pitch to be varied. The horizontal hinge pin 14*a* provides the mounting for pressure plate 16 and force transducer 16*a* thereby uncoupling the prior art reliance on and practice of taking force measurements from the vertical pin. This unique method of taking force measurements from the horizontal pin itself provides a more accurate measurement of force as it relates purely to propulsion.

In the preferred example, the lower part of the oar clamp 10*a* is fitted with a cam follower 24 in contact with the cam 20. The cam is secured to the vertical pin 13 by the angular reference 18. The profile of the cam 20 allows the pitch to be precisely varied as the oar traverses the stroke from catch to finish. Preferably, there are also replaceable bushes 13*a* and 13*b* to eliminate any free play of the vertical pivot 12 when rotating about the vertical pin 13. The cam can easily be changed to suite individual crew. The vertical reference is also used by a transducer module 5 located in the base of the vertical pivot 12 to indicate the position of the gate as it swivels about the vertical pin 13.

As shown in FIG. 1, in one embodiment of the present invention, the bottom face of the oar clamp 10 is fitted with a horizontal reference plate or transducer 22 that allows the horizontal angle and/or force of the oar to be measured. However, those skilled in the art would appreciate that the horizontal reference plate 22 could be replaced with, or adapted in conjunction with, a vertical reference plate or transducer (not shown) fitted to the oar clam 10 so as to measure the vertical angle and/or force of the oar.

The electronic circuitry and batteries are contained in the removable compartment 26, facilitating charging and software upgrades.

It is envisaged that coaches will be able to upload a crew's performance data and have cams custom designed to maximize the crew's performance.

Figure 3:
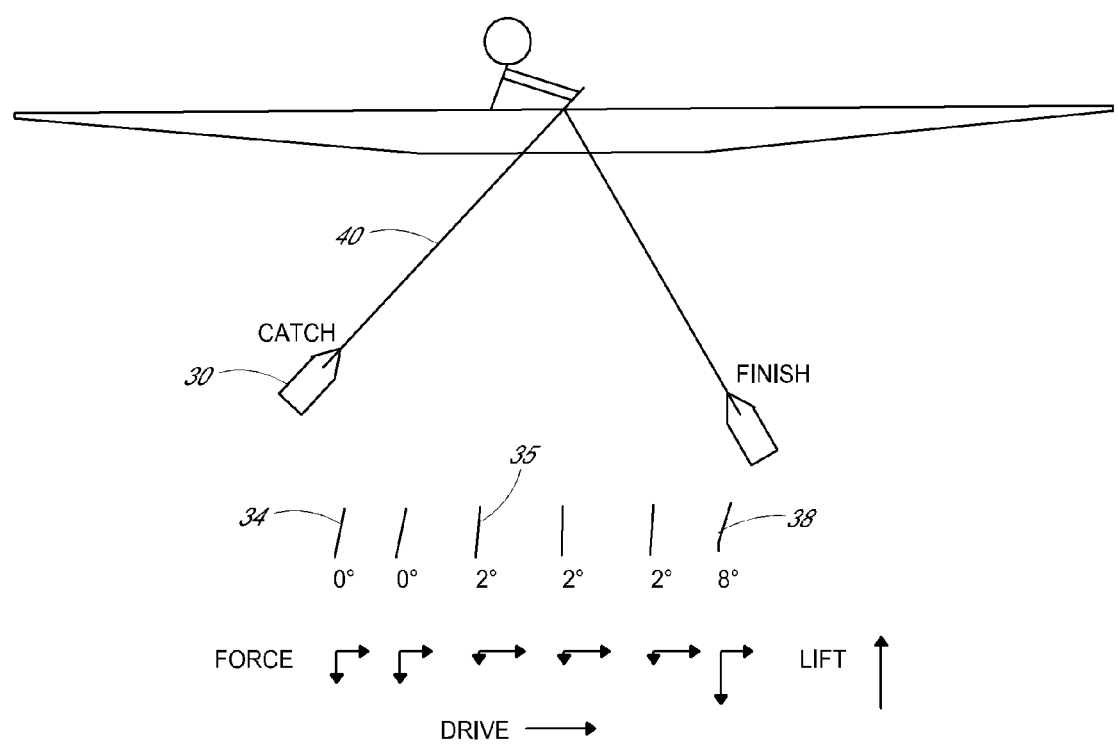
FIG. 3 shows a schematic representation of oar blade pitch variation in using the invention.

Referring now to FIG. 3 there is shown a schematic drawing of oar blade pitch variation on using the rowlock. As the oar blade 40 enters the water, also known as the 'catch' 30, it is angled at 6 degrees pitch 34 relative to the vertical. This contributes to a lift component. As the rower pulls through the power stroke 36, or 'drive', the blade is at 2 degrees of pitch. As the oar blade 'exits' the water at the end of the rowing stroke 38 at 8 degrees pitch, there is also a lift component present which impinges on the back of the blade.

It is obvious that by carefully designing the cam, not only can maximum forward propulsion be achieved but also the potential exists to add a lift component to the beginning and end of the stroke. Providing lift will also reduce surface area contact and reduce drag with a resultant increase in boat speed. The increased pitch at the exit 38 also aids in the extraction of the blade from the water by the rower. This reduces the potential to slow the boat by reducing the drag of the oar in the water.

The combined measurement and consequent adjustments will allow crews or coaches to fine tune the boat to the crew. With approximately 200 stokes in a race a 1% efficiency improvement will relate to a significant racing advantage.

Those skilled in the art will readily appreciate that while the foregoing has been given by way of illustrative example of this invention, all such and other modifications and variations thereto as would be apparent to persons skilled in the art are deemed to fall within the broad scope and ambit of this invention as is herein set forth.

Moreover, in the specification the terms "comprising" and "containing" shall be understood to have a broad meaning similar to the term "including" and will be understood to imply the inclusion of a stated integer or step or group of integers or steps but not the exclusion of any other integer or step or group of integers or steps. This definition also applies to variations on the terms "comprising" and "containing" such as "comprise", "comprises", "contain" and "contains".

The invention claimed is:

1. A variable pitch oarlock of a rowing shell, comprising:
an oar clamp adapted to secure an oar; a vertical pin adapted to permit the oarlock to swivel about a rigger of the rowing shell; and
a horizontal hinge or pivot between the oar clamp and a vertical bearing assembly to thereby permit the oar clamp to pivot in the horizontal plane and to swivel about the vertical pin, wherein during a rowing stroke oar blade pitch is both variable and accurately measureable and wherein the horizontal hinge or pivot is further configured to provide a mounting for a force sensor, the force sensor configured to measure horizontal forces during the rowing stroke; and
wherein the oar clamp further comprises a cam follower in contact with a cam or spacer having a specific profile, which is adapted to affect the horizontal displacement of the oar clamp, and wherein in operation the cam or spacer having the specific profile is configured to allow the vertical angular displacement of the oar clamp to be precisely set thereby controlling blade angle at all phases of the rowing stroke.

2. The variable pitch oarlock of claim 1, wherein the cam or spacer having the specific profile is interchangeable with one or more cams having different profiles selected according to a desired blade pitch pattern or to suit performance of an individual rower.

3. A method of coaching or training rowing crew, comprising:
measuring force, angle and depth using the variable pitch oarlock of claim 1;
analyzing the measurements of force, angle and depth;
interchanging a cam with a cam having a different profile to adjust the boat for maximum performance for the particular crew; and
designing a coaching or training schedule according to an analysis of the measurements of force, angle and depth.

4. A variable pitch oarlock system, comprising: the variable pitch oarlock of claim 1, wherein the horizontal pivot means comprises a hinge pin; and one or more force transducers connected to the hinge pin, the one or more force transducers configured to obtain force measurements and configured to enable propulsive force measurement in the absence of hydrodynamic lift or oar weight.

5. A method of coaching or training rowing crew, comprising:
measuring force, angle and depth using the variable pitch oarlock system of claim 4;
analyzing the measurements of force, angle and depth; interchanging a cam with a cam having a different profile to adjust the boat for maximum performance for the particular crew; and
designing a coaching or training schedule according to an analysis of the measurements of force, angle and depth.

* * * * *